United States Patent [19]

Cooper et al.

[11] Patent Number: 5,304,665
[45] Date of Patent: Apr. 19, 1994

[54] PROCESS FOR THE PREPARATION OF HIGHLY ESTERIFIED ALKOXYLATED POLYOL COMPOSITIONS

[75] Inventors: Charles F. Cooper, Paoli, Pa.; Bernard C. Sekula, High Bridge, N.J.; Stephen D. Harper, West Chester, Pa.

[73] Assignees: Arco Chemical Technology, L.P., Wilmington, Del.; CPC International, Inc., Englewood Cliffs, N.J.

[21] Appl. No.: 43,431

[22] Filed: Apr. 5, 1993

[51] Int. Cl.$^5$ .............................................. C07C 51/367
[52] U.S. Cl. ...................................... 554/149; 554/148
[58] Field of Search ............................................ 554/149

[56] References Cited

U.S. PATENT DOCUMENTS

| | | | |
|---|---|---|---|
| 2,610,125 | 9/1952 | Valko | 426/611 |
| 2,678,935 | 5/1954 | Sundberg et al. | 554/149 |
| 3,337,595 | 8/1967 | Lamont | 554/227 |
| 3,435,024 | 3/1969 | Nobile et al. | 536/18.2 |
| 4,022,808 | 5/1977 | Yoshihara et al. | 554/149 |
| 4,115,415 | 9/1978 | Yoshihara et al. | 554/149 |
| 4,464,182 | 8/1984 | Tack et al. | 44/393 |
| 4,600,539 | 7/1986 | Hoppe et al. | 514/785 |
| 4,681,900 | 7/1987 | Iwasaki | 514/786 |
| 4,687,843 | 8/1987 | Smolin et al. | 536/18.3 |
| 4,849,242 | 7/1989 | Kekshner | 426/601 |
| 4,861,613 | 8/1989 | White et al. | 426/611 |
| 4,983,329 | 1/1991 | Cooper | 554/172 |
| 5,059,443 | 10/1991 | Ennis et al. | 426/531 |
| 5,077,073 | 12/1991 | Ennis et al. | 426/531 |
| 5,175,323 | 12/1992 | Cooper | 554/164 |

FOREIGN PATENT DOCUMENTS

| | | |
|---|---|---|
| 660601 | 7/1965 | Belgium . |
| 564516 | 3/1951 | Canada . |
| 89105357.1 | 10/1989 | European Pat. Off. . |
| 0516099 | 12/1992 | European Pat. Off. . |
| 1595369 | 4/1970 | Fed. Rep. of Germany . |
| 207070 | 2/1984 | Fed. Rep. of Germany . |
| 49-10433 | 3/1974 | Japan . |
| 55-79313 | 6/1980 | Japan . |
| 55-160710 | 12/1980 | Japan . |
| WO93/04030 | 3/1993 | PCT Int'l Appl. . |
| 2129004 | 5/1984 | United Kingdom . |

*Primary Examiner*—Paul J. Killos
*Assistant Examiner*—Dwayne C. Jones
*Attorney, Agent, or Firm*—Stephen D. Harper

[57] ABSTRACT

A convenient method of obtaining useful highly esterified alkoxylated polyol fat substitutes from readily available triglycerides such as fats and oils is provided.

20 Claims, No Drawings

5,304,665

PROCESS FOR THE PREPARATION OF HIGHLY ESTERIFIED ALKOXYLATED POLYOL COMPOSITIONS

FIELD OF THE INVENTION

This invention relates to methods for obtaining highly esterified alkoxylated polyol compositions useful as reduced calorie fat substitutes from naturally occurring triglycerides such as fats and oils.

BACKGROUND OF THE INVENTION:

A wide variety of substances have been proposed for use as fat substitutes in food compositions. The chemical structures of such substances are selected such that they are more resistant to breakdown by the metabolic processes of the human digestive system which normally occur upon ingestion of conventional triglyceride lipids. Because of their increased resistance to digestion and absorption, the number of calories per gram available from the fat substitutes is considerably reduced as compared to common vegetable oils, animal fats, and other lipids. The use of such substances thus enables the preparation of reduced calorie food compositions useful in the control of body weight.

U.S. Pat. No. 4,861,613 describes one class of particularly useful fat substitutes wherein-a polyol such as glycerin is alkoxylated with an epoxide such as propylene oxide and then esterified with any of a number of fatty acids or fatty acid equivalents to form an esterified alkoxylated polyol. Generally speaking, it is desirable to accomplish nearly complete esterification (i.e., to react at least 90% of the hydroxyl groups of the alkoxylated polyol intermediate with fatty acid). These substances have the physical and organoleptic properties of conventional triglyceride lipids, yet are significantly lower in available (absorbed) calories than edible oils owing to their pronounced resistance towards pancreatic lipase enzymatic hydrolysis. The thermal and oxidative stability of the esterified alkoxylated polyols renders them especially suitable for use in the preparation of reduced calorie food compositions requiring exposure to high temperatures.

The methods developed to date for the preparation of esterified alkoxylated polyol fat substitutes of this type have largely required multi-step procedures when a naturally occurring triglyceride is to be utilized as the source of the long chain acyl groups incorporated into the esterified alkoxylated polyol. The triglyceride is first hydrolytically split into glycerin (which may be employed as the polyol component) and a mixture of fatty acids. The fatty acids (after separation from the glycerin) may be used directly without further modification as described in U.S. Pat. No. 4,983,329. Alternatively, the fatty acids prior to use in an esterification reaction with an alkoxylated polyol may be converted into $C_1$-$C_4$ alkyl esters (as described in U.S. Pat. Ser. No. 5,175,232) or fatty acid halides (as described in U.S. Pat. No. 4,861,613). The alkoxylated polyol must first be prepared by reacting an epoxide with a polyol such as glycerin, sugar alcohol, glycoside, monosaccharide, disaccharide or other organic compound having two or more hydroxy groups. While such multi-step procedures work well and afford esterified alkoxylated polyols suitable for use as fat substitutes, the number of steps involved, including both synthetic and purification steps, renders these substances considerably more costly than the triglycerides on which they are based. Since the esterified alkoxylated polyol is intended to entirely or substantially replace conventional high caloric triglycerides in food compositions and since certain types of food compositions will normally contain high levels of fat or oil, it is apparent there exists a great need for improved processes whereby the manufacturing cost of esterified alkoxylated polyols may be substantially reduced.

Although the direct esterification method as described hereinabove and in U.S. Pat. No. 4,983,329 has the advantage of utilizing free fatty acids, thus avoiding the necessity of first preparing alkyl ester or halide derivatives prior to the alkoxylated polyol esterification step, it is not an ideal method. In particular, direct esterification normally is optimally carried out under conditions such that the water generated by the reaction of fatty acid and alkoxylated polyol is continuously removed from the reaction mixture by means such as distillation (which may be under vacuum) or sparging with an inert gas such as nitrogen. Substantially complete esterification is difficult to achieve unless the water is so removed since esterification is an equilibrium reaction. Under typical reaction conditions, the free fatty acids which are present will have a tendency to steam distill together with the water and consequently be removed from the reaction zone. This adversely affects the rate of the desired esterification reaction, not only because the fatty acid is a required reactant but also because such esterifications are preferably conducted in the absence of any metallic catalysts (due to difficulties in removing such catalysts, many of which are highly toxic, after completion of esterification) using an excess of fatty acid to self-catalyze the esterification. If fatty acid is being continually lost from the reaction zone due to overhead losses, fresh fatty acid must be added to maintain the desired rate of reaction. The need to use make-up quantities of fatty acid and to recycle, recover, or otherwise dispose of the fatty acid lost overhead increases the overall cost of such a process. Another problem is that the presence of large quantities of free fatty acid during the entire time necessary to convert an alkoxylated polyol containing no acyl groups initially to a completely esterified product provides an opportunity for the fatty acids to dimerize, polymerize, oxidize, or otherwise degrade. These undesired side-reactions of the fatty acid may result in the formation of acidic or unpleasant-tasting or smelling impurities which are difficult to remove by standard edible oil refining techniques such as deodorization, hydrogenation, or bleaching. The development of synthetic procedures which would alleviate the aforesaid difficulties would therefore be a highly desirable improvement in the fat substitute art.

SUMMARY OF THE INVENTION

This invention provides a process for preparing a highly esterified alkoxylated polyo, composition having a ratio of $$\frac{\text{moles acyl groups}}{\text{moles acyl groups plus moles hydroxy groups}}$$

(also referred to as "degree of esterification") greater than 0.90, more preferably, greater than 0.95. An epolide, presence of a catalytic amount of polyalcohol are reacted in the nd for a time and at a an alkali metal or alkaline earth compound temperature effective to accomplish ring-opening of the epoxide and formation of a partially esterified alkoxylated polyol composition. The molar ratio of epoxide to the combined amount of triglyceride and aliphatic polyalcohol is at least 1:1 to 64:1. The molar ratio of triglyceride: aliphatic polyalcohol is at least 1:3/m wherein m is the number of hydroxy groups in the aliphatic polyalcohol and is an integer of from 2 to 8.

The partially esterified alkoxylated polyol composition is contacted with a fatty acid for a time and at a temperature effective to provide the highly esterified alkoxylated polyol composition. The number of moles of fatty acid is at least equal to the number of moles of hydroxy groups in the partially esterified alkoxylated polyol composition.

The method of the present invention represents a vastly streamlined route to highly esterified alkoxylated polyol fat substitute and offers a number of advantages as compared to previously known methods, including, for example, minimization of the total amount of free fatty acid required. The quantity of triglyceride which must be hydrolytically split in an initial step is thereby reduced. The level of residual acidity present in the final product which is not removable by conventional oil processing techniques also quite unexpectedly tends to be reduced from the levels observed when a non-esterified alkoxylated polyol is reacted with excess fatty acid. A smaller total volume of fatty acid is lost overhead during operation of the process of this invention; raw material, waste disposal, and recycle costs are thereby significantly diminished.

DETAILED DESCRIPTION OF THE INVENTION

The triglyceride component which is necessary for the practice of this invention may be any synthetic or naturally-occurring fatty acid triester of glycerin. Such substances will typically correspond to the general structure

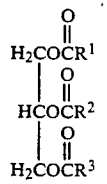

wherein $R^1$, $R^2$, and $R^3$ are the same or different and are $C_5$-$C_{23}$ saturated or unsaturated, linear or branched hydrocarbyl groups (i.e., moieties comprised of carbon and hydrogen atoms) The glycerin may be esterified, for example, with any $C_6$-$C_{24}$ fatty acid such as caproic acid, caprylic acid, pelargonic acid, capric acid, undecylic acid, lauric acid, palmitic acid, margeric acid, stearic acid, nonadecylic acid, arachidic acid, behenic acid, lignoceric acid, lauroleic acids, myristoleic acids, palmitoleic acids, oleic acid, elaidic acid, godoleic acid, gondoic acids, cetoleic acid, linoleic acid, linolenic acid, eleostearic acids, and mixtures thereof. Suitable triglycerides are preferably edible oils and fats and include, for example, the triesters of glycerin obtained from natural lipids such as cottonseed oil, soybean oil, peanut oil, olive oil, safflower oil, rapeseed oil (preferably, low erucic rapeseed oil or fully hydrogenated high erucic rapeseed oil), fish oils, sunflower oil, palm oil, palm kernel oil, tallow, lard, coconut oil, sesame oil, corn oil, and fully or partially hydrogenated derivatives thereof.

The epoxide to be reacted with the triglyceride may be any organic compound containing a three-membered cyclic ether (oxirane) group and advantageously is a $C_2$-$C_{10}$ aliphatic epoxide. Illustrative epoxides which may be utilized in the instant process include ethylene oxide, propylene oxide, cis- or trans 2,3-butylene oxide, 1,2-butylene oxide, isobutylene oxide, 1-pentene oxide, cyclohexene oxide, cyclooctene oxide, 1-octene oxide, styrene oxide, allyl glycidyl ether, phenyl glycidyl ether, methyl glycidyl ether, ethyl glycidyl ether, epichlorohydrin, and the like and mixtures thereof. Due to their low cost, high reactivity, and favorable impact on esterified alkoxylated polyol fat substitute properties, the use of ethylene oxide, propylene oxide, 1,2-butylene oxide, or mixtures thereof is especially desirable. The epoxide ring is opened during the process of this invention to afford oxyalkylene units having the general skeletal formula —C—C—O— containing two carbon atoms and one oxygen atom. The oxyalkylene units may be substituted with hydrogen, alkyl, aryl, aralkyl, or other such substituents. In a preferred embodiment, the oxyalkylene units correspond to the structure

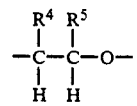

wherein $R^4$ and $R^5$ are the same or different and are hydrogen or a $C_1$-$C_6$ alkyl group such as methyl, ethyl, propyl, isopropyl, butyl, sec-butyl, iso-butyl, tert-butyl, pentyl, hexyl, cyclohexyl, and the like. Most preferably, one of $R^4$ or $R^5$ is methyl and the other R group is hydrogen. In one desirable embodiment, $R^5$ in the oxyalkylene units adjacent to the acyl groups in the final esterified alkoxylated polyol is a $C_1$-$C_6$ alkyl group since secondary ester linkages resistant to enzymatic hydrolysis upon ingestion are thereby furnished.

The amount of epoxide reacted and incorporated into the partially esterified alkoxylated polyol will be selected so as to provide a molar ratio of epoxide: (triglyceride and aliphatic polyalcohol) of from 1:1 to 64:1. When the aliphatic polyalcohol is glycerin, trimethyl propane, 1,2,6-trihydroxyhexane or other trihydric alcohol, it will generally be advantageous to keep the molar ratio in the range of from 3:1 to 20:1. The physical properties and organoleptic qualities of the final highly esterified alkoxylated polyol product may be controlled as desired by varying the amount of epoxide used relative to the amount of triglyceride and aliphatic polyalcohol. For example, when the epoxide is propylene oxide, increasing the aforementioned ratio will tend to lower the melting point of the esterified alkoxylated polyol.

The other necessary components for practice of the present invention are an alkali metal or alkaline earth and an aliphatic polyalcohol. The alkali metal is most preferably potassium or sodium. If an alkaline earth is employed, the alkaline earth is most desirably barium or calcium. Potassium will typically be preferred over the other possible alkali metals or alkaline earths owing to the high rate of reaction and minimal formation of by-products observed. The aliphatic polyalcohol (which preferably contains primary or secondary hydroxyl groups and no tertiary hydroxyl groups) may be selected from $C_2$-$C_{10}$ aliphatic diols (e.g., ethylene glycol, propylene glycol, 1,3-propanediol, 1,4-butanediol, 1,2- butanediol, 2,3-butanediol, pinacol, 1,2-cyclohexanediol, 1,2-pentanediol, 1,4-pentanediol, 1,5-pentanediol, 2,4-pentanediol, 3,3-dimethyl-1,2-butanediol, 2-ethyl-2-methyl-1,2-propanediol, 1,2-hexanediol, 1,5-hecanediol, 1,6-hexanediol, 1,7-heptanediol, 2-ethyl-2-(hydroxymethyl)-1,3propanediol, 1,1,1-tris(hydroxymethyl)ethane, 1,2,6-trihydroxyhexane, 1,2,3-heptanetriol, and the like), pentaerythritol, sugar alcohols [including those compounds corresponding to the formula HOCH$_{22}$(CHOH)$_n$CH$_2$OH wherein n is 2 to 6 such as erythritol, xylitol, sorbitol, arabitol, mannitol, and the like], monosaccharides (e.g., erythrose, threose, ribose, arabinose, xylose, lyxose, allose, altrose, glucose, mannose, gulose, idose, galactose, fructose, galactose, and the like), disaccharides (e.g., sucrose, lactose, maltose) and alkyl glycosides (e.g., methyl glycosides, ethyl glycosides, propyl glycosides, and other glycoside molecules wherein the alkyl glycoside is an acetal formed by interaction of a C$_1$-C$_{20}$ alcohol with a carbonyl group of a mono- or disaccharide such as glucose). Also suitable for use as the aliphatic polyalcohol are relatively low molecular weight alkoxylated adducts of the aforementioned C$_2$-C$_{10}$, aliphatic diols, C$_3$-C$_{12}$ aliphatic triols, pentaerythritol, sugar alcohols, monosaccharides, disaccharides, and alkyl glycosides, especially the ethoxylated, propoxylated, and butoxylated adducts having number average molecular weights of from 106 to 500. Examples of such adducts include, but are not limited to, propoxylated glycerin, diethylene glycol, tripropylene glycol, propoxylated sucrose, ethoxylated trimethylal propane, and the like. Also suitable for use as the aliphatic polyalcohol are hydroxy-containing substances such as tetrahydrofuran oligomers, oxetane oligomers, glycerol oligomers, alkoxylated glycerol oligomers, and the like.

The aliphatic polyalcohol will typically contain from 2 to 8 hydroxy groups, which normally will be present as free hydroxy groups (e.g., —OH) or, if the aliphatic polyalcohol is converted into an alkali metal or alkaline earth salt, may have an alkoxide structure(e.g., —OM, where M=alkali metal, alkaline earth). However, some of the hydroxy groups may be present as "masked" hydroxy groups wherein the hydroxy group is substituted with a base-labile functional group such as acyl (e.g.,

which is removed or transferred under the conditions of the process of this invention, provided that at least one of the hydroxy groups is a free (non-masked) hydroxy group.

For example, the aliphatic polyalcohol may be a mono- or di-ester of glycerin (i.e., a mono- or diglyceride) or any other incompletely esterified polyol such as a partially esterified sugar alcohol, saccharide, diol, triol, tetrol, alkyl glycoside or the like. The ester group may be either a short, medium, long, branched, or linear chain, saturated or unsaturated, ester functionality, but preferably is a fatty acid ester group. Mono-and diglycerides and polyols partially substituted with fatty acid ester groups are well-known in the art and may be readily obtained from triglycerides by the direct condensation of fats or fatty acids with glycerin or a similar polyol at an elevated temperature. For example, the process described in British Pat. No. 421,063 may be utilized wherein triglyceride is reacted with the alkali metal salt of glycerin or the like to afford a mixture of the alkali metal salts of mono- and diglycerides. monoglycerides may be substituted in the 1 or 2 position, while the diglycerides may be 1,3- or 1,2-substituted. Mixtures of various di- and monoglycerides together with glycerol may be utilized to advantage as the aliphatic polyalcohol in the process of this invention.

The alkali metal or alkaline earth present is believed to function as a catalyst and will generally initially be present in association with the aliphatic polyalcohol so as to form a salt of the aliphatic polyalcohol. Free aliphatic polyalcohol may still additionally be present.

In general, higher rates of reaction will be attained as the ratio of alkali metal or alkaline earth to aliphatic polyalcohol is increased. The preparation of alkali metal and alkaline earth salts of aliphatic polyalcohols is well-known in the art. For example, the aliphatic polyalcohol may be contacted with an alkali metal or alkaline earth hydroxide, methoxide, or ethoxide and then subjected to vacuum distillation so as to remove water, methanol, or ethanol to form the desired salt. Alternatively, the aliphatic polyalcohol may be reacted with alkali metal (which may be in the form of a solid dispersion or liquid alloy) or alkali metal hydride to form the salt with liberation of hydrogen gas. Generally speaking, the amount of alkali metal or alkaline earth present will preferably be from about 250 to 10,000 parts per million (more preferably, from about 500 to 5000 ppm) based on the total weight of triglyceride, epoxide, and aliphatic polyalcohol.

Since the alkali metal or alkaline earth salt of the aliphatic polyalcohol may be a solid, relatively high melting substance with only limited solubility in the other components of the reaction, the process of this invention may be conveniently carried out by forming the salt in situ. For example, the reactor vessel may be initially charged with a mixture of the triglyceride and aliphatic polyol. An alkali metal or alkaline earth hydroxide or alkoxide such as sodium hydroxide, potassium hydroxide, barium hydroxide, calcium hydroxide, sodium methoxide, potassium methoxide, sodium ethoxide, potassium t-butoxide, or the like is then added and a vacuum applied so as to remove the water or alcohol generated by the formation of the salt of the aliphatic polyalcohol. Such conditions are selected so as to avoid taking the aliphatic polyalcohol overhead. The water or alcohol could alternatively be removed by azeotropic distillation using an appropriate azeotropic agent. Alternatively, an alkali metal or alkaline earth hydride or an alkali metal in metallic form such as sodium hydride, potassium hydride, calcium hydride, sodium metal, potassium metal, or sodium-potassium alloy could be added so as to react with the aliphatic polyalcohol to form the salt and hydrogen as a by-product, which can be readily removed from the reaction mixture by sparging with an inert gas. This method provides an aliphatic polyalcohol salt in dispersed or dissolved form in a matrix of triglyceride (mono- and di-glycerides will typically also be simultaneously generated), thus avoiding the handling problems which may otherwise be associated with utilizing the salt in isolated form.

It is important that the ratio of the number of moles of triglyceride to the number of moles of aliphatic polyalcohol is at least 1:3/m wherein m is the number of hydroxy groups in the aliphatic polyalcohol. For example, when glycerin (m=3) is used as the aliphatic polyalcohol, this molar ratio must be at least 1:1. Controlling the relative amounts of these two components in this manner leads to the generation of a partially esterified alkoxylated polyol wherein at least 50% of the end groups in the intermediate are long chain (fatty) acyl groups. The remaining end groups will generally be unesterified hydroxy groups arising from ring-opening addition of the epoxide on the aliphatic polyol and/or glycerol moiety of the triglyceride. The aforementioned molar ratio is preferably less than 200: 3/m since higher ratios may lead to impracticably long reaction times and the generation of undesired by-products. Moreover, when the ratio is greater than 9:3/m and the process is reduced under the conditions described in application Ser. No. 08/044,446, filed Apr. 5, 1993, entitled "Process for the Preparation of Highly tsterified Alkoxylated Polyol Compositions" (agent's docket no. PF 01-2210A), the product obtained will typically be at least 90% esterified and thus directly suitable for use as a reduced calorie fat substitute without the need to carry out a subsequent esterification step. However, if desired, the process of the instant invention may be performed using a ratio greater than 9:3/m and the intermediate product more completely esterified to a suitable extent.

The temperature at which the triglyceride, epoxide, and aliphatic polyalcohol are reacted in the presence of the alkali metal or alkaline earth is not critical, but should be selected so as to be sufficiently high to provide a relatively rapid rate of epoxide ring-opening and yet not so high as to generate undesirable by-products such as low molecular weight unsaturated polyesters. Typically, suitable temperatures will be in the range of from 50° C. to 200° C. When propylene oxide, ethylene oxide, and/or 1,2-butylene oxide are utilized as the epoxide and the catalyst earth is sodium or potassium it is preferred to operate in the range of 80° C. to 150° C.

The reaction mixture is held at the selected temperature or within the selected temperature range for a period of time sufficiently long so as to accomplish the desired degree of epoxide conversion, which will generally be at least 75% of the epoxide charged and more preferably is at least 90% of the epoxide charged. Reaction times of from about 0.5 hours to 24 hours will typically suffice for this purpose, but will be dependent on variables such as epoxide reactivity, temperature, alkali metal or alkaline earth concentration, and the like. Optimum reaction times may be readily determined by routine experimentation.

If desired, an inert organic solvent may additionally be present in the reaction mixture so as to dissolve certain of the reaction components, provide effective heat transfer and temperature control, or reduce viscosity. Suitable organic solvents will generally be non-protic substances (i.e., compounds without active hydrogens) such as aromatic hydrocarbons, aliphatic hydrocarbons, halogenated hydrocarbons, ethers, and the like. However, by selecting reactants which are liquid or dissolved in each other at the reaction temperature, the need for a solvent may be eliminated, thereby simplifying the recovery and purification of the product. The reaction is most preferably carried out under an inert (oxygen-free) atmosphere in the absence of water or active hydrogen-containing compounds other than the aliphatic polyalcohol, as the presence of such substances may detrimentally affect the quality of the partially esterified alkoxylated polyol. The pressure during the reaction is not critical and may typically be maintained between 0.5 atmospheres and 20 atmospheres. If a relatively volatile epoxide is employed, it will generally be advantageous to use a closed pressurizable reaction vessel so that the bulk of the epoxide may be maintained as a liquid phase in the reactor.

The foregoing step of this invention may be carried out in a continuous, semicontinuous, or batch manner using any appropriately configured reactor capable of heating and mixing the reactor contents. Although all of the epoxide may be combined with the triglyceride and aliphatic polyalcohol at the beginning of the reaction, it will usually be advantageous to add the epoxide in an incremental fashion to a stirred mixture of the triglyceride and aliphatic polyalcohol at temperature. Epoxide addition under these conditions will tend to yield a more uniform distribution of oxyalkylene units among the different branches or arms of the partially esterified alkoxylated polyol and a high degree of triglyceride conversion. This incremental epoxide addition will typically be performed over a 0.5 to 12 hour period, with subsequent soak time to accomplish substantially complete conversion of the epoxide. If more than one epoxide is utilized, the different epoxides may be added as a mixture or sequentially. By adding ethylene oxide first followed by propylene oxide, the esterified polyoxyalkylene block copolymers of the type described in European Pat. Pub. No. 481,717 may be prepared, for example.

When the reaction of the epoxide, triglyceride, and aliphatic polyalcohol has proceeded to the extent desired to form the partially esterified alkoxylated polyol intermediate, the alkali metal or alkaline earth present may (if desired) be removed by any appropriate method. For example, the reaction product can be contacted with a particulate absorbent such as magnesium silicate or aluminum silicate at an appropriate temperature (typically, 50° C. to 150° C.) so as to absorb the alkali metal or alkaline earth onto the absorbent and then filtered. Small amounts of water may be added so as to enhance absorption efficiency. Alternatively, the reaction product can be treated with an acid such as a mineral acid (e.g., hydrochloric acid, sulfuric acid, phosphoric acid) or an organic acid (e.g., acetic acid, oxalic acid, citric acid, tartaric acid) so as to form a precipitate which can be removed by filtration. Treatment with an appropriate ion exchange resin or extraction with water, dilute aqueous acid, or a polar solvent such as methanol or the like may also be utilized.

Alternatively, however, the crude partially esterified alkoxylated polyol may be carried forward to the subsequent esterification step without purification or removal of the alkali metal or alkaline earth. It has been surprisingly found that the presence of these substances does not adversely affect the desired addition of acyl groups onto the remaining hydroxy groups of the intermediate and that, in fact, the alkali metal or alkaline earth may under certain conditions actually help catalyze the esterification. The final highly esterified alkoxylated polyol may thereafter be treated using any of the procedures described hereinabove in order to separate the alkali metal or alkaline earth and to provide an essentially neutral and metal-free product suitable for use in food compositions.

In the subsequent esterification step, the partially esterified alkoxylated polyol intermediate is contacted with a fatty acid for a time and at a temperature effective to provide the desired highly esterified alkoxylated polyol composition. In order to accomplish complete or substantially complete esterification, the number of moles of fatty acid utilized must be at least equal to the number of moles of hydroxy groups in the partially esterified alkoxylated polyol composition. Although the esterification could be catalyzed using a strong acid such as a sulphonic acid, sulfuric acid, phosphorus pentoxide, hypophosphoric acid, or a cationic exchange resin or a transition metal species (preferably, a Lewis acid) such as tin chloride, titanium alkoxide, aluminum or nickel alloys, zinc chloride or the like, preferably no added catalyst is employed since it is difficult to remove all traces of such catalysts from the esterification product. In addition, the strongly acidic catalysts may cause darkening of the reaction mixture or the dehydration of hydroxy-containing species. Where no added catalyst is present, the esterification preferably is self-catalyzed using a slight to moderate excess of fatty acid. In this embodiment, the number of moles of fatty acid is preferably from $1.05 \times m \times$ moles of aliphatic polyalcohol to $1.40 \times m \times$ moles of aliphatic polyalcohol (where m is equal to the number of hydroxyl groups on the aliphatic polyalcohol).

The fatty acid is preferably a $C_6$–$C_{24}$ saturated or unsaturated fatty acid and may be either linear or branched in structure. Such substances may be readily obtained from natural sources by the well-known hydrolytic splitting (hydrolysis) of the triglycerides found in edible fats and oil. The fat or oil may be fully or partially hydrogenated prior to splitting. Alternatively, the fatty acids may be hydrogenated after hydrolysis. A single fatty acid or a mixture of different fatty acids may be used. Illustrative examples of suitable fatty acids include, but are not limited to, caprylic acid, caproic acid, capric acid, lauric acid, myristic acid, palmitic acid, palmitoleic acid, stearic acid, oleic acid, elaidic acid, linoleic acid, linolenic acid, arachidic acid, gadoleic acid, behenic acid, lignoceric acid, and the like.

In order to achieve a relatively rapid rate of esterification while avoiding problems with dehydration of the partially esterified alkoxylated polyol, oxidation of the reaction components, or other undesired side reactions, it is generally desirable to carry out the esterification at a temperature of from 150° C. to 275° C. (more preferably, 180° C. to 240° C.) and in the substantial absence of molecular oxygen. The esterification rate can be suitably enhanced by providing a means for remove or binding the water generated during esterification so as to drive the reaction to completion or near completion, For example, a reduced pressure of from about 0.01 mm up to atmospheric (more preferably, from 1 to 50 mm) may be utilized to take the water overhead. An inert gas such as nitrogen, helium, an aliphatic hydrocarbon, carbon dioxide or the like may be sparged or passed through the reaction mixture in order to remove the water as it is formed. Azeotropic distillation of the water with a suitable azeotropic agent (entrainer) such as an aliphatic or aromatic hydrocarbon will also be effective for this purpose. The use of molecular sieves or other water absorbing or reactive substances may also be helpful in reducing the reaction time required to achieve a high degree of hydroxy group conversion. The conditions for water removal are selected such that a minimum amount of fatty acid is taken overhead. Typically, reaction times of from 0.5 to 18 hours will be sufficient to provide substantially complete esterification.

Once the desired degree of esterification has been accomplished, any residual unreacted fatty acid should be removed from the highly esterified alkoxylated polyol composition so as to lower the acidity to a level which will be acceptable in food applications. Suitable methods include vacuum steam stripping (distillation) at an elevated temperature (as described, for example, in U.S. Pat. No. 4,983,329), alkali neutralization to precipitate fatty acid salts which may then be removed by filtration, extraction (with methanol, for example), and dilution with a solvent such as hexane in which the desired product is soluble and the fatty acid is insoluble reduced by filtration.

The reduced calorie fat substitute produced by the process of this invention can be additionally purified or treated so as to render it more suitable for use in food compositions using any of the techniques known in the art for refining natural vegetable or animal oils and fats. Such techniques include, but are not limited to, degumming, bleaching, filtration, deodorization, hydrogenation, dewaxing, and the like. Various additives such as stabilizers, anti-oxidants, vitamins and so forth can also be incorporated into the esterified alkoxylated polyol.

Highly esterified alkoxylated polyo, compositions produced in accordance with this invention can replace, in full or in part, conventional edible oils or fats in a cooking oil, frying oil, salad oil, Or shortening, for example, Additional uses include combining the reduced calorie fat substitutes with other foodstuff ingredients to form foods such as frozen deserts (e.g., sherbert, ice cream, frozen yogurt, milk shakes), baked goods (cakes, doughnuts, muffins, brownies, breads, pies, rolls, pastries, cookies, biscuits, crackers)o nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels), fried foods (fried poultry, fritters, fried pies, fried vegetables such as french fried potatoes, fried fish), reformed and comminuted meats (lunch meats, sausage, hot dogs, hamburger), pet food, meat and egg substitutes or extenders, whipped toppings, gravies and other sauces, frostings, fillings, icings, cocoa butter replacements or blends, candies (especially those normally containing fatty ingredients such as chocolate or peanut butter), soups and dry baking mixes (for muffins, cakes, pancakes, waffles, brownies, and the like). Owing to the fat-like properties and stability of the highly esterified alkoxylated polyols, minimum reformulation of standard foods will generally be required. The viscosity, melting profile, yield point, hardness, thixotropic area, liquid/solid stability, solid fat index, and other physical properties of the reduced calorie fat substitute are preferably selected by manipulation of the chemical structures and relative proportions of the individual starting materials of the process such that the product mimics as closely as possible the analogous properties of the conventional triglyceride being replaced.

Illustrative ingredients which may be used in combination with the highly esterified alkoxylated polyol compositions obtainable by practice of this invention include carbohydrates (flour, starches, sugars, celluloses, polydextrose or other bulking agents), edible lipids (triglycerides), proteins (from animal or vegetable sources) vitamins, antioxidants, emulsifiers, thickeners, preservatives, colorants, flavors, fragrances, sugar substitutes (saccharin, aspartame, sucralose, cyclamates, and the like), other fat substitutes or fat mimetics (for example, sucrose polyester or caprenin), water, milk, spices, eggs and the like. Oil-in-water or water-in-oil emulsions can be readily prepared by combining water, the reduced calorie fat substitute, and (optionally) other ingredients such as emulsifiers. The reduced calorie fat substitutes of this invention are particularly suitable for the preparation of foods requiring exposure to elevated temperatures. Unlike other proposed fat substitutes such as proteinaceous macrocolloids or certain polysaccharide-based substances requiring water to render them fat-like in texture, the esterified alkoxylated polyols produced by this invention are exceptionally stable thermally and do not readily decompose or lose their fat-like properties when heated. The compositions thus may readily be utilized in deep fat frying applications to prepare fried foods such as savory snacks, fried chicken, fried fish, french fries, and the like since they will function as effective heat transfer media (that is, they will transmit heat rapidly and uniformly to the food being fried and also provide crispness).

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

A suitably sized stainless steel autoclave is charged with olive oil (735 parts by weight) and the monopotassium salt of glycerin (22 parts by weight; prepared by contacting 1 equivalent of glycerin with 1 equivalent of potassium hydroxide and heating under vacuum until all water has been removed). The contents of the autoclave are sealed under a nitrogen atmosphere and heated to 100° C. Propylene oxide (290 parts by weight) is added by continuous feed at a rate so as to maintain an autogenous pressure of 50-60 psig. After addition is completed, the reaction product is heated at 100° C. until at least 95% propylene oxide conversion is accomplished. The partially esterified alkoxylated polyol thus obtained is expected to be equivalent to the esterified alkoxylated polyol prepared by reacting olive oil fatty acids (commercial oleic acid) with 290 parts by weight of a propoxylated glycerin (ave. no. of moles propylene oxide per mole of glycerin=5) until the hydroxyl value is 27 mg KOH/G. Approximately 80% of the end groups in the partially esterified alkoxylated polyol are estgr groups, with the remaining 20% being hydroxy groups.

The partially esterified alkoxylated polyol prepared as described hereinabove (100 parts by weight) is treated with magnesium silicate to remove residual potassium, filtered, combined with olive oil fatty acids (20 parts by weight), and heated at 230° C. for 7 hours using a nitrogen purge to remove water from the reaction vessel. Overhead loss of fatty acid is only 0.3% of the amount charged to the vessel. No make-up acid is added. Approximately 90% of the end groups in the highly esterified alkoxylated polyol product are ester groups, as determined by high pressure liquid chromatography with the remaining 10% being hydroxyl groups. A small sample of the product is purified by caustic refining and found to have an acidity level after potassium removal of 0.2%.

EXAMPLE 2

The partially esterified alkoxylated polyol prepared in Example 1 is treated with magnesium silicate, filtered, combined with 20.0 parts of olive oil fatty acids, and heated at 250° C. for 7 hours using a nitrogen purge to remove water from the reaction vessel. No make-up acid is added. Greater than 95% of the end groups in the highly esterified alkoxylated polyol product are ester groups, as determined by high pressure liquid chromatography, with the remaining groups being hydroxy groups. The product is purified by vacuum steam stripping to remove excess fatty acid and to provide a reduced calorie fat substitute suitable for use in a food composition.

COMPARATIVE EXAMPLE 3

To demonstrate the advantages of the process of this invention, a direct esterification of propoxylated glycerin (containing ca. 5 equivalents of propylene oxide per equivalent of glycerin) is performed. A mixture of propoxylated glycerin (382 parts by weight) and olive oil fatty acids (1050 parts) is heated at 250° C. under a nitrogen purge to remove water from the reaction vessel. Make-up acid (30 parts by weight) is added during the esterification to maintain a relatively constant reaction rate. Heating is discontinued when 95% conversion of the hydroxy groups in the propoxylated glycerin to ester groups is accomplished. A minimum of 2% of the initial fatty acid charge is lost overhead. After refinement, the highly esterified alkoxylated polyol has an acid value of 0.3%.

EXAMPLES 4-14

These examples illustrate the use of a number of different triglycerides, epoxides, aliphatic polyalcohols, alkali metals, alkaline earths, and fatty acid sources in the process of this invention. The procedures described in Example 1 are generally followed with the substitutions noted in Table I. Esterification is continued until at least 90-95% esterification is achieved. In Examples 4, 8, and 12, the esterification is carried out under a vacuum of 10 mm Hg in order to remove the water generated.

TABLE I

| Example No. | Triglyceride | pbw$^x$ | Epoxide | pbw | M$^y$ | ppm$^z$ |
| --- | --- | --- | --- | --- | --- | --- |
| 4 | corn oil | 1000 | ethylene oxide | 660 | K | 2000 |
| 5 | soybean oil | 1000 | 1-butene oxide | 360 | Na | 4000 |
| 6 | hydrogenated high erucic rapeseed oil | 1000 | EO/PO$^p$ | 248 | Ba | 7500 |
| 7 | canola oil | 1000 | 1-pentene oxide | 546 | Ca | 6000 |
| 8 | cottonseed oil | 1000 | PO/BO$^q$ | 828 | K | 1500 |
| 9 | sunflower seed oil | 1000 | EO/PO$^r$ | 481 | K | 3000 |
| 10 | partially hydrogenated soybean oil | 1000 | propylene oxide | 2030 | Na | 3500 |
| 11 | fully hydrogenated soybean oil | 1000 | ethylene oxide | 715 | Na | 2500 |
| 12 | safflower seed oil | 1000 | PO/EGE$^s$ | 443 | K | 2500 |
| 13 | tallow | 1000 | PO/OO$^t$ | 386 | Ca | 8000 |
| 14 | lard | 1000 | propylene oxide | 624 | Na | 4500 |

TABLE I-continued

| Example No. | Aliphatic Polyalcohol | pbw | Temp., °C. | Fatty acid | % Excess | Temp., °C. |
|---|---|---|---|---|---|---|
| 4 | 1,2,6-trihydroxy hexane | 67 | 115 | a | 5 | 225 |
| 5 | pentaerythritol | 13.6 | 120 | b | 10 | 235 |
| 6 | trimethylol propane | 26.8 | 150 | c | 15 | 200 |
| 7 | 1,4-butanediol | 29.5 | 135 | d | 20 | 250 |
| 8 | 2,3-butanediol | 14.7 | 90 | e | 25 | 210 |
| 9 | sorbitol | 12.1 | 100 | f | 30 | 190 |
| 10 | tripropylene glycol | 144 | 125 | g | 35 | 180 |
| 11 | propoxylated glycerin[l] | 22.2 | 110 | h | 0[u] | 150 |
| 12 | mono- + di-glycerides[m] | 38 | 80 | i | 0[v] | 175 |
| 13 | propoxylated sucrose[n] | 32.2 | 130 | j | 20 | 230 |
| 14 | glycerol oligomer[o] | 18 | 100 | k | 5[w] | 150 |

Footnotes to Table I
[a]mixture of fatty acids obtained by hydrolytic splitting of corn oil
[b]stearic acid
[c]mixture of fatty acids obtained by hydrolytic splitting of palm oil
[d]mixture of fatty acids obtained by hydrolytic splitting of palm kernel oil
[e]mixture of fatty acids obtained by hydrolytic splitting of coconut oil
[f]lauric acid
[g]mixture of fatty acids obtained by hydrolytic splitting of partially hydrogenated soybean oil (iodine value = 50)
[h]mixture of fatty acids obtained by hydrolytic splitting of fully hydrogenated soybean oil (iodine value <5)
[i]mixture of fatty acids obtained by hydrolytic splitting of tallow
[j]mixture of fatty acids obtained by hydrolytic splitting of canola oil (low erucic rapeseed oil)
[k]mixture of fatty acids obtained by hydrolytic splitting of cocoa butter
[l]3 equivalents of propylene oxide per equivalent of glycerin
[m]glycerin monostearate and glycerin distearate (molar ratio ca. 2:1)
[n]8 equivalents of propylene oxide per equivalent of sucrose, prepared as described in U.S. Pat. No. 2,908,681 (Anderson et al.)
[o]triglycerol, prepared by adaptation of the method described in PCT Appl. WO 91/10368 published July 25, 1991
[p]mixture of 132 parts by weight ethylene oxide and 116 parts by weight propylene oxide
[q]mixture of 684 parts by weight propylene oxide and 144 parts by weight 1-butene oxide
[r]44 parts by weight ethylene oxide added first, followed by 437 parts by weight propylene oxide
[s]mixture of 290 parts by weight propylene oxide and 153 parts by weight ethyl glycidyl ether
[t]mixture of 232 parts by weight propylene oxide and 154 parts by weight 1-octene oxide
[u]3000 ppm SnCl$_2$
[v]5000 ppm ZnCl$_2$
[w]5000 ppm p-toluene sulfonic acid
[x]parts by weight
[y]alkali metal or alkaline earth
[z]parts by million, based on the combined weight of triglyceride, epoxide, and aliphatic polyalcohol

We claim:

1. A process for preparing a highly esterified alkoxylated polyol composition having a degree of esterification greater than 0.90, said process comprising
    (a) contacting an epoxide, an aliphatic polyalcohol, and a triglyceride in the presence of a catalytic amount of a catalyst selected from alkali metals and alkaline earths for a time and at a temperature of from 50° C. to 200° C. to accomplish ring-opening of the epoxide and formation of a partially esterified alkoxylated polyol composition, wherein the molar ratio of epoxide: (triglyceride+aliphatic polyalcohol) is from 1:1 to 65:1 and the molar ratio of triglyceride: aliphatic polyalcohol is at least 1:3/m wherein m is the number of hydroxy groups in the aliphatic polyalcohol and is a integer of from 2 to 8; and
    (b) contacting the partially esterified alkoxylated polyol composition with a fatty acid for a time and at a temperature effective to provide the highly esterified alkoxylated polyol composition, the number of moles of fatty acid being at least equal to the number of moles of hydroxy groups in the partially esterified alkoxylated polyol composition.

2. The process of claim 1 wherein the number of moles of fatty acid utilized in step (b) is from 1.05×m× moles of aliphatic polyalcohol to 1.40×m×moles of aliphatic polyalcohol.

3. The process of claim 1 wherein the partially esterified alkoxylated polyol is treated to remove the catalyst prior to step (b).

4. The process of claim 1 wherein the triglyceride is obtained from a lipid selected from the group consisting of corn oil, soybean oil, peanut oil, cottonseed oil, rapeseed oil, sunflower seed oil, safflower seed oil, sesame oil, tallow, lard, fish oil, cocoa butter, milk fat, coconut oil, olive oil, palm oil, palm kernel oil, mixtures thereof, partially hydrogenated derivatives thereof, and fully hydrogenated derivatives thereof.

5. The process of claim 1 wherein the epoxide is a $C_2$-$C_{10}$ aliphatic epoxide.

6. The process of claim 1 wherein the aliphatic polyalcohol is selected from the group consisting of $C_2$-$C_{10}$ aliphatic diols, $C_3$-$C_{12}$ aliphatic triols, pentaerythritol, sugar alcohols, monosaccharides, disaccharides, glycerol oligomers, and alkyl glycosides, and alkoxylated derivatives thereof having number average molecular weights of from 106 to 500.

7. A process of claim 1 wherein the catalyst is an alkali metal selected from sodium and potassium.

8. The process of claim 1 wherein step (b) is carried out under conditions effective to remove water formed by said contacting of the partially esterified alkoxylated polyol composition and the fatty acid.

9. The process of claim 1 wherein the highly esterified alkoxylated polyol composition is steam distilled at subatmospheric pressure after step (b) to remove unreacted fatty acid.

10. The process of claim 1 wherein the temperature in step (a) is from 50 to 200° C.

11. The process of claim 1 wherein the temperature in step (b) is from 150° C. to 275° C.

12. The process of claim 1 wherein step (b) is performed in the absence of an added catalyst.

13. A process for preparing a highly esterified alkoxylated polyol composition having a degree of esterification of greater than 0.95, said process comprising
    (a) contacting a $C_2$-$C_{10}$ aliphatic epoxide, an aliphatic polyalcohol, and a triglyceride in the presence of from 250 to 10,000 ppm of an alkali metal at a temperature of from 50° C. to 200° C. for a time effective to accomplish ring-opening of the $C_2$-$C_{10}$ aliphatic epoxide and formation of a partially esterified alkoxylated polyol composition, wherein the molar ratio of epoxide:(triglyceride+aliphatic polyalcohol) is from 3:1 to 20:1 and the molar ratio of triglyceride:aliphatic polyalcohol is from 1: 3/m to 19: 3/m wherein m is the number of hydroxy group in the aliphatic polyalcohol and is an integer of from 2 to 4; and (b) contacting the partially esterified alkoxylated polyol composition with a fatty acid at a temperature of from 150° C. to 275° C. for a time effective to provide the highly esterified alkoxylated polyol composition, the number of moles of fatty acid being from $1.05 \times m \times$ moles of aliphatic polyalcohol to $1.40+m+$ moles of aliphatic polyalcohol.

14. The process of claim 13 wherein the $C_2$-$C_{10}$ aliphatic epoxide is selected from ethylene oxide, propylene oxide, 1,2-butylene oxide, and mixtures thereof.

15. The process of claim 13 wherein the aliphatic polyalcohol is selected from the group consisting of $C_2$-$C_{10}$ aliphatic diols, $C_3$-$C_{12}$ aliphatic triols, pentaerythritol, sugar alcohols having 4 hydroxy groups, monosaccharides having 4 hydroxy groups, alkyl glycosides having 4 hydroxy groups, diglycerol, and alkoxylated derivatives thereof having molecular weights of from 106 to 500.

16. The process of claim 13 wherein the aliphatic polyalcohol is a mono or diglyceride.

17. The process of claim 13 wherein the alkali metal is potassium.

18. The process of claim 13 wherein the triglyceride is obtained from a lipid selected from the group consisting of corn oil, soybean oil, peanut oil, cottonseed oil, rapeseed oil, sunflower seed oil, safflower seed oil, sesame oil, tallow, lard, fish oil, milk fat, cocoa butter, coconut oil, olive oil, palm oil, palm kernel oil, partially hydrogenated derivatives thereof, fully hydrogenated derivatives thereof, and mixtures thereof.

19. The process of claim 13 wherein the alkali metal is present in step (a) at a concentration of from 750 ppm to 5000 ppm.

20. A process for preparing a highly esterified alkoxylated polyol composition having a degree of esterification of greater than 0.95, said process comprising
(a) contacting an epoxide selected from ethylene oxide, propylene oxide, 1,2 butylene oxide, and mixtures thereof, an aliphatic triol, and a triglyceride in the presence of from 750 to 5000 ppm of sodium or potassium, at a temperature of from 75° C. to 190° C. for a time effective to accomplish ring-opening of the epoxide and formation of a partially esterified alkoxylated polyol composition, wherein the molar ratio of epoxide: (triglyceride+aliphatic triol) is from 3:1 to 25:1 and the molar ratio of triglyceride: aliphatic triol is from 3:1 to 19:1; and
(b) contacting the partially esterified alkoxylated polyol composition with a $C_6$-$C_{24}$ saturated or unsaturated monocarboxylic acid at a temperature of from 180° C. to 240° C. for a time effective to provide the highly esterified alkoxylated polyol composition, the number of moles of acid being from $3.15 \times$ the number of moles of aliphatic triol to 4.20 x the number of moles of aliphatic triol.

* * * * *